US011234968B2

(12) United States Patent
Yan et al.

(10) Patent No.: US 11,234,968 B2
(45) Date of Patent: Feb. 1, 2022

(54) USE OF VCP INHIBITOR AND ONCOLYTIC VIRUS IN THE PREPARATION OF AN ANTI-TUMOR DRUG

(71) Applicant: Guangzhou Virotech Pharmaceutical Co., Ltd., Guangdong (CN)

(72) Inventors: Guangmei Yan, Guangzhou (CN); Haipeng Zhang, Guangzhou (CN); Yuan Lin, Guangzhou (CN); Suizhen Lin, Guangzhou (CN); Jing Cai, Guangzhou (CN); Shoufang Gong, Guangzhou (CN); Jun Hu, Guangzhou (CN); Xiao Xiao, Guangzhou (CN); Kai Li, Guangzhou (CN); Jiankai Liang, Guangzhou (CN); Yaqian Tan, Guangzhou (CN); Wenbo Zhu, Guangzhou (CN); Wei Yin, Guangzhou (CN)

(73) Assignee: Guangzhou Virotech Pharmaceutical Co., Ltd., Guangdong (CN)

( * ) Notice: Subject to any disclaimer, the term of this patent is extended or adjusted under 35 U.S.C. 154(b) by 7 days.

(21) Appl. No.: 16/325,960

(22) PCT Filed: Aug. 18, 2017

(86) PCT No.: PCT/CN2017/097969
§ 371 (c)(1),
(2) Date: Feb. 15, 2019

(87) PCT Pub. No.: WO2018/033126
PCT Pub. Date: Feb. 22, 2018

(65) Prior Publication Data
US 2019/0167641 A1 Jun. 6, 2019

(30) Foreign Application Priority Data
Aug. 18, 2016 (CN) .......................... 201610688100.7

(51) Int. Cl.
| *A61K 31/00* | (2006.01) |
| *A61K 31/4439* | (2006.01) |
| *A61K 31/444* | (2006.01) |
| *C12N 7/00* | (2006.01) |
| *A61K 31/4178* | (2006.01) |
| *A61P 35/00* | (2006.01) |
| *A61K 35/768* | (2015.01) |
| *A61K 45/06* | (2006.01) |
| *A61K 48/00* | (2006.01) |
| *A61K 9/00* | (2006.01) |
| *A61K 9/19* | (2006.01) |
| *A61K 9/48* | (2006.01) |
| *A61K 9/70* | (2006.01) |
| *A61K 31/519* | (2006.01) |
| *A61K 31/7105* | (2006.01) |

(Continued)

(52) U.S. Cl.
CPC ........ *A61K 31/4178* (2013.01); *A61K 9/0019* (2013.01); *A61K 9/19* (2013.01); *A61K 9/48* (2013.01); *A61K 9/7023* (2013.01); *A61K 31/00* (2013.01); *A61K 31/4439* (2013.01); *A61K 31/519* (2013.01); *A61K 35/768* (2013.01); *A61K 45/06* (2013.01); *A61K 48/00* (2013.01); *A61P 35/00* (2018.01); *C12N 7/00* (2013.01); *A61K 31/713* (2013.01); *A61K 31/7105* (2013.01); *A61K 38/1774* (2013.01); *C12N 2770/36132* (2013.01)

(58) Field of Classification Search
None
See application file for complete search history.

(56) References Cited

U.S. PATENT DOCUMENTS

2010/0247622 A1   9/2010 Coffey et al.
2010/0266618 A1*  10/2010 Stojdl ................ G01N 33/5011
                                                  424/174.1

(Continued)

FOREIGN PATENT DOCUMENTS

| CN | 101820892 A | 9/2010 |
| CN | 104814984 A | 8/2015 |
| CN | 105456302 A | 4/2016 |

(Continued)

OTHER PUBLICATIONS

Lin et al. Identification and characterization of alphavirus M1 as a selective oncolytic virus targeting ZAP-defective human cancers. P.N.A.S., 2014, 111: E4504-E4512.*
Office Action dated Mar. 24, 2020 in Japanese Application No. 2019-509470.
Wang et al., "Inhibition of p97-dependent Protein Degradation by Eeyarestatin I", The Journal of Biological Chemistry, vol. 283, No. 12, pp. 7445-7454, 2008 (10 pages total).
Vekaria et al., "Targeting p97 to Disrupt Protein Homeostasis in Cancer", Frontiers in Oncology, vol. 6, Article 181, pp. 1-8, 2016 (8 pages total).

(Continued)

Primary Examiner — Nianxiang Zou
(74) Attorney, Agent, or Firm — Sughrue Mion, PLLC

(57) ABSTRACT

The present invention belongs to the field of biomedicine and relates to use of VCP (valosin-containing protein, VCP) inhibitor and oncolytic virus in the preparation of an anti-tumor drug. The present invention firstly discovers that VCP inhibitor can be used in the preparation of an anti-tumor synergist for oncolytic virus. Meanwhile, the present invention relates to a pharmaceutical composition comprising VCP inhibitor and oncolytic virus, a pharmaceutical kit comprising VCP inhibitor and oncolytic virus, and use of VCP inhibitor and oncolytic virus for treating tumor, especially a tumor that is not sensitive to oncolytic virus. The present invention also relates to an anti-tumor administration system, characterized in that, comprising oncolytic virus and a reagent for detecting the expression level of VCP.

12 Claims, 10 Drawing Sheets

Specification includes a Sequence Listing.

(51) Int. Cl.
  *A61K 31/713* (2006.01)
  *A61K 38/17* (2006.01)

(56) References Cited

U.S. PATENT DOCUMENTS

2012/0316198 A1* 12/2012 Wiestner .............. A61P 17/00
  514/309
2017/0304380 A1   10/2017 Yan et al.

FOREIGN PATENT DOCUMENTS

| CN | 106177961 A | 12/2016 |
| WO | 2016/029833 A1 | 3/2016 |
| WO | 2018/033126 A1 | 2/2018 |

OTHER PUBLICATIONS

Deshaies, "Proteotoxic crisis, the ubiquitin-proteasome system, and cancer therapy", BMC Biology, vol. 12, No. 94, pp. 1-14, 2014 (14 pages total).
Lin et al., "Identification and characterization of alphavirus M1 as a selective oncolytic virus targeting ZAP-defective human cancers", PNAS, Oct. 6, 2014, pp. E4504-E4512.
Quetglas et al., "Alphavirus vectors for cancer therapy", Virus Research, vol. 153, 2010, pp. 179-196.
Communication dated Jul. 23, 2019 by the European Patent Office in application No. 17841098.1.
Daniel Anderson, et al., "Targeting the AAA ATPase p97 as an Approach to Treat Cancer through Disruption of Protein Homeostasis", Cancer Cell, Nov. 9, 2015, pp. 653-665, vol. 28.
Christopher W. Valle, et al., "Critical Role of VCP/p97 in the Pathogenesis and Progression of Non-Small Cell Lung Carcinoma", PLoS One, Dec. 2011, 12 pages, vol. 6, Iss. 12.
Shinji Yamamoto, et al., "Elevated Expression of Valosin-Containing Protein (p97) in Hepatocellular Carcinoma is Correlated With Increased Incidence of Tumor Recurrence", Journal of Clinical Oncology, Feb. 1, 2003, pp. 447-452, vol. 21, No. 3.
Yuichi Tsujimoto, et al., "Elevated Expression of Valosin-Containing Protein (p97) is Associated with Poor Prognosis of Prostate Cancer", Clinical Cancer Research, May 1, 2004, pp. 3007-3012, vol. 10.
Kai Li, et al., "Activation of Cyclic Adenosine Monophosphate Pathway Increases the Sensitivity of Cancer Cells to the Oncolytic Virus M1", Molecular Therapy, Jan. 2016, pp. 156-165, vol. 24, No. 1.
China Office Action for Application No. 201610688100.7 dated Mar. 9, 2017.
China Office Action for Application No. 201610688100.7 dated Sep. 29, 2017.
Taiwan Office Action for Application No. 106128179 dated Jul. 4, 2018.
Taiwan Office Action for Application No. 106128179 dated Dec. 18, 2018.
International Search Report for PCT/CN2017/097969 dated Nov. 22, 2017 [PCT/ISA/210].
Written Opinion for PCT/CN2017/097969 dated Nov. 22, 2017 [PCT/ISA/237].
Communication dated May 12, 2020, from the European Patent Office in Application No. 17 841 098.1.
2nd Non-Final Notice of Decision of Refusal dated Dec. 1, 2020 from the Japanese Patent Office in JP Application No. 2019-509470.

\* cited by examiner

USE OF VCP INHIBITOR AND ONCOLYTIC VIRUS IN THE PREPARATION OF AN ANTI-TUMOR DRUG

CROSS REFERENCE TO RELATED APPLICATIONS

This application is a National Stage of International Application No. PCT/CN2017/097969, filed Aug. 18, 2017, claiming priority based on Chinese Patent Application No. 201610688100.7, filed Aug. 18, 2016.

TECHNICAL FIELD

The present disclosure relates to the field of biomedicine and to the use of VCP protein inhibitor, oncolytic virus, or its combination such as in the preparation of an anti-tumor drug.

BACKGROUND

Oncolytic virus refers to a class of replicatable viruses that can infect and kill tumor cells. Some oncolytic viruses can selectively infect cancer cells over normal cells with little or no infection of normal cells. Some oncolytic viruses can infect cancer cells and normal cells, but exhibit greater or faster lethality against the cancer cells. Oncolytic virotherapy, being an innovative strategy for a tumor targeted therapy, can use a natural or genetically modified virus (or combination thereof) to infect tumor cells and replicates said virus in the tumor cells, so as to achieve the effect of dissolving and killing the tumor cells, preferably in a targeted way, and preferably with little or no damage to normal cells.

M1 virus (Alphavirus M1) belongs to the genus Alphavirus, and M1 virus can have potential application in the preparation of an anti-tumor drug. For example, Chinese invention patent application No. 201410425510.3 discloses that M1 virus could selectively cause the death of tumor cells without affecting the survival of normal cells, so that it has potential application in the anti-tumor field. Nevertheless, different tumors show different sensitivity to the M1 virus. For certain tumors, M1 virus, when being administered alone, does not exhibit a satisfactory oncolytic effect. According to the Chinese invention patent application No. 201410425510.3, incorporated herein by reference for its discussion of treatment of tumors with M1 virus and other viruses and for its discussion of different outcomes for different tumor types and treatment levels/methodologies, it is disclosed that M1 present different efficacy when treating different tumor type. When used for treating pancreatic cancer, nasopharyngeal carcinoma, prostate cancer and melanoma, it presents a most effective result. When used for treating colorectal cancer, liver cancer, bladder cancer and breast cancer, it is less effective than the previous mentioned type. When used for treating glioma, cervical cancer, lung cancer, it is even less effective. When used for treating gastric cancer, it presents a least effective result.

The screening of the compounds that increase therapeutic effect of oncolytic virus on tumor is underway to identify compounds that can increase the anti-tumor spectrum and anti-tumor strength of oncolytic virus. Chinese patent CN 201510990705.7 previously submitted by the inventor discloses that chrysophanol and its derivatives are used as anti-tumor synergists for M1 virus, and a combination of both could reduce the survival rate of tumor cells to 39.6%. However, the mechanism of action of this combination has not previously been described, and it can be desirable to achieve higher anti-tumor strength of virus-synergists combinations and/or to achieve lower or no effect on normal cells, and/or to use a combination with a better understood mechanism of action.

SUMMARY

Provided is a use of VCP inhibitor in the preparation of an anti-tumor synergist for oncolytic virus.

Also provided is an anti-tumor pharmaceutical composition that enables oncolytic virus to exhibit better anti-tumor effect, such as increased lethality and/or reduced side-effects.

Also provided is a synergistic anti-tumor drug combination with oncolytic virus, and which is preferably directed to tumors that are not sensitive to oncolytic virus.

Also provided is an individualized administration system and method.

Also provided is a method of treatment of a solid or hematological (i.e. blood) tumor that include administration of the foregoing therapeutic combinations.

The present disclosure describes synergists and synergist-virus combinations that can demonstrate an effective and/or safe therapy for cancer.

DETAILED DESCRIPTION

Terms

Figure 1:
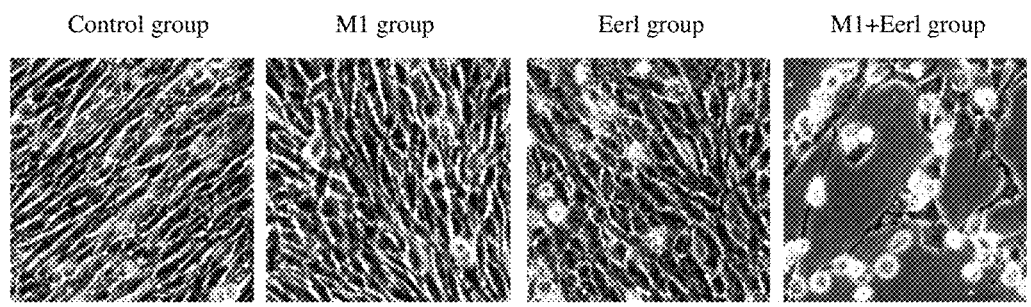
FIG. 1 shows photographs of microscopic views of sections of liver cells subject to different treatments.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Use of words such as "approximate", "about", "substantially", etc. modifies the value/description as would be understood by a person of skill in the art based upon the context and the parameter being described, and where further guidance is needed in order to be understood, a value of 5% can be applied. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example." Described percent sequence identity refers to the percentage of nucleic acid or amino acid residues within a given DNA, RNA or protein, respectively, that are identical to the reference sequence.

In case of conflict, the present specification, including explanations of terms, will control. In addition, all the materials, methods, and examples are illustrative and not intended to be limiting.

VCP Inhibitors

It has been found that VCP inhibitors can enhance the oncolytic effect of oncolytic virus. Suitable VCP inhibitors can operate by way of reducing the activity of VCP (such as the ATPase activity), by degrading the VCP protein and/or by reducing the expression of VCP by the cell.

VCP (valosin containing protein, VCP), also called P97, is an ATPase that is widely expressed in many cells. It serves as an important element in the endoplasmic reticulum stress-associated degradation pathways and is responsible for recognizing and presenting ubiquitinated proteins and delivering them to proteasome for degradation, so as to ensure protein homeostasis in cells. It has been reported in several articles (1, 2) that VCP is expressed highly in tumor cells, and inhibiting VCP can significantly induce the death of tumor cells.

In some embodiments, an interference fragment (Si RNA) of VCP was used to inhibit the expression of the gene, thereby reducing the expression amount of the corresponding protein. The result shows that neither inhibition nor non-inhibition of VCP expression alone cause pathological change to cell morphology. Also, use of M1 virus alone did not cause pathological change of cell morphology. However, a combination of the inhibition of VCP expression and the application of M1 virus caused pathological change of cell morphology.

Further, as discussed herein, the oncolytic effect of an oncolytic virus can be significantly enhanced by inhibiting VCP. As disclosed herein, the combination of a compound that inhibits the activity of VCP, such as Eeyarestatin I, NMS-873 or CB-5083, with oncolytic virus, such as M1 virus, can be used to attack tumor cells. The result shows that the anti-tumor effect can be enhanced by combining Eeyarestatin I, NMS-873 or CB-5083 or combination thereof with oncolytic virus.

The present disclosure in some embodiments uses a VCP inhibitor that can be used as an anti-tumor synergist and/or as a drug-resistance reversal agent for oncolytic virus.

A drug-resistance reversal agent means that, when using oncolytic virus serving as an antitumor drug for treating a tumor that is not sensitive to oncolytic virus, or that is found to be resistance to oncolytic virus, then VCP inhibitor can be used as a oncolytic virus resistance reversal agent, to be used in combination with a oncolytic virus, to reverse the resistance ability of the tumor.

The present disclosure in some embodiments uses a VCP inhibitor in the preparation of an anti-tumor synergist/a drug-resistance reversal agent for oncolytic virus.

Suitable VCP inhibitors can include (but is not limited to) a compound that inhibits the activity of VCP protein, such as Eeyarestatin I (Formula 1), NMS-873 (Formula 2) or CB-5083 (Formula 3). VCP inhibitor that can be used as an oncolytic synergist, such as described herein, can be obtained by any suitable method, such as chemical synthesis, separation from biological materials, biotechnical methods, etc.

In some examples of the present invention, the VCP protein inhibitor can be Eeyarestatin I, NMS-873, CB-5083 or combination thereof.

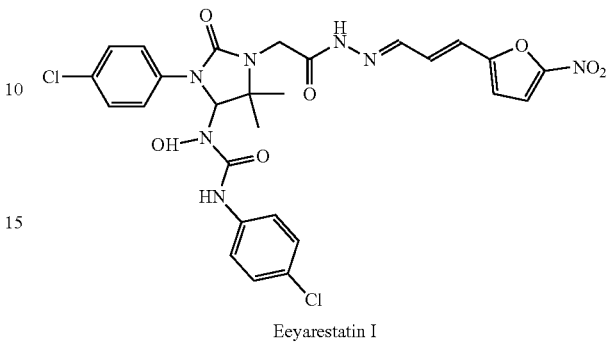

Eeyarestatin I

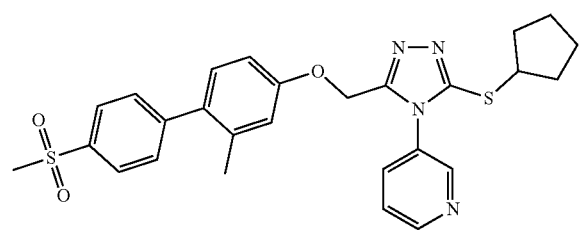

NMS-873

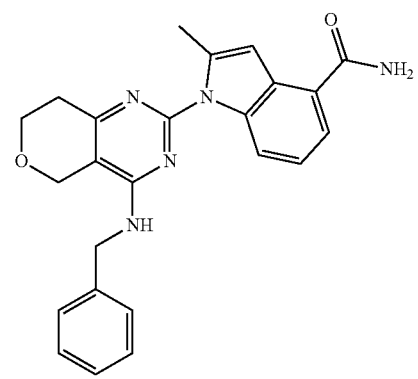

CB-5083

In some embodiments, a VCP inhibitor can comprise a compound that inhibits the activity of VCP protein. In some embodiments, a VCP inhibitor can comprise or consist of or consist essentially of Eeyarestatin I, NMS-873 or CB-5083 or a combination thereof, preferably Eeyarestating I, NMS-873 or combinations thereof. In some embodiments, a genetic tool for inhibiting the expression of VCP gene can comprise RNA for RNA interference (RNAi), microRNA, gene editing or gene knockout agent.

A VCP inhibitor can also include a genetic-based tool for inhibiting the expression of VCP gene, including but not limited to means such as use of RNA interference (RNAi), microRNA and gene editing or knockout.

The VCP inhibitor also includes, for example, small inhibitory nucleic acid molecules, such as short interfering RNA (siRNA), double-stranded RNA (dsRNA), micro-RNA (miRNA), ribozyme, and short hairpin RNA (shRNA), that decrease or ablate expression of VCP.

Such small inhibitory nucleic acid molecules may comprise a first and a second strand that hybridize to each other to form one or more double-stranded regions, each strand being about 18 to about 28 nucleotides in length, about 18 to about 23 nucleotides in length, or about 18, 19, 20, 21 or 22 nucleotides in length. Alternatively, a single strand may contain regions therein capable of hybridizing to each other to form a double-stranded region, such as in shRNA molecules.

Such small inhibitory nucleic acid molecules may also comprise modified nucleotides, while maintaining an ability to reduce or ablate VCP expression. The modified nucleotides may be included to improve in vitro or in vivo characteristics, such as stability, activity, and/or bioavailability. For example, such small inhibitory nucleic acid molecules may comprise modified nucleotides as a percentage of the total number of nucleotides present in the siRNA molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified nucleotides). Such modified nucleotides may comprise, for example, deoxynucleotides, 2'-O-methyl nucleotides, 2'-deoxy-2'-fluoro nucleotides, 4'-thionucleotides, locked nucleic acid (LNA) nucleotides, and/or 2'-O-methoxyethyl nucleotides. The small inhibitory nucleic acid molecules, such as siRNAs, may also contain a '5- and/or a 3'-cap structure, to prevent degradation by exonucleases.

In some embodiments, the small inhibitory nucleic acid molecules comprise double-stranded nucleic acids containing blunt ends, or overhanging nucleotides. Other nucleotides present may comprise, for example, nucleotides that result in mismatches, bulges, loops, or wobble base pairs. The small inhibitory nucleic acid molecules may be formulated for administration, for example, by encapsulation in liposomes, or by incorporation into other vehicles, such as biodegradable polymers, hydrogels, or cyclodextrins.

In various embodiments, said VCP inhibitor can serve as a substance (for example, compounds, amino acid sequences, or nucleotide sequences) or genetic tool for knocking down or affecting the gene expression of VCP or reducing the protein amount or protein activity of VCP. Those skilled in the art could modify, replace and/or change these compounds or genetic tools as the inhibitors, provided that the resulting substance has the effect of inhibiting VCP.

In another embodiment of the present invention, the VCP protein inhibitor can be an interference RNA fragment of VCP, or an antibody against VCP.

In a preferred embodiment of the present invention, the VCP protein inhibitor is an interference RNA fragment of VCP, or an antibody against VCP. In some embodiments, the VCP inhibitor is effective against, designed to target, produced or raised using, or is specific for, VCP set forth in NCBI Gene ID: 7415. In other embodiments, the VCP inhibitor is effective against, designed to target, produced or raised using, or is specific for, a variant of the VCP set forth in NCBI Gene ID: 7415. The variant VCP protein may have, for example, an amino acid sequence that is at least 80%, at least 85%, at least 90%, at least 91%, at least 92%, at least 93%, at least 94%, at least 95%, at least 96%, at least 97%, at least 98%, or at least 99%, identical to the VCP protein set forth in NCBI Gene ID: 7415.

In some embodiments, the VCP inhibitor is an antibody. The antibody may be a monoclonal antibody, a polyclonal antibody, a multivalent antibody, a multispecific antibody (e.g., bispecific antibody), and/or an antibody fragment that binds to VCP. The antibody may be a chimeric antibody, a humanized antibody, a CDR-grafted antibody, or a human antibody, for example. The antibody fragment may be, for example, a Fab, Fab', F(ab')2, Fv, Fd, single chain Fv (scFv), disulfide bond Fv (sdFv), or a VL or a VH domain. The antibody may be in the form of a conjugate, for example, conjugated to a tag, a detectable label, or a cytotoxic agent. The antibody may be of the isotype IgG (e.g., IgG1, IgG2, IgG3 or IgG4), IgA, IgM, IgE or IgD.

The VCP inhibitor also includes, for example, small inhibitory nucleic acid molecules, such as short interfering RNA (siRNA), double-stranded RNA (dsRNA), micro-RNA (miRNA), ribozyme, and short hairpin RNA (shRNA), that decrease or ablate expression of VCP.

Such small inhibitory nucleic acid molecules may comprise a first and a second strand that hybridize to each other to form one or more double-stranded regions, each strand being about 18 to about 28 nucleotides in length, about 18 to about 23 nucleotides in length, or about 18, 19, 20, 21 or 22 nucleotides in length. Alternatively, a single strand may contain regions therein capable of hybridizing to each other to form a double-stranded region, such as in shRNA molecules.

Such small inhibitory nucleic acid molecules may also comprise modified nucleotides, while maintaining an ability to reduce or ablate VCP expression. The modified nucleotides may be included to improve in vitro or in vivo characteristics, such as stability, activity, and/or bioavailability. For example, such small inhibitory nucleic acid molecules may comprise modified nucleotides as a percentage of the total number of nucleotides present in the siRNA molecule, such as at least about 5%, 10%, 15%, 20%, 25%, 30%, 35%, 40%, 45%, 50%, 55%, 60%, 65%, 70%, 75%, 80%, 85%, 90%, 95% or 100% modified nucleotides). Such modified nucleotides may comprise, for example, deoxynucleotides, 2'-O-methyl nucleotides, 2'-deoxy-2'-fluoro nucleotides, 4'-thionucleotides, locked nucleic acid (LNA) nucleotides, and/or 2'-O-methoxyethyl nucleotides. The small inhibitory nucleic acid molecules, such as siRNAs, may also contain a '5- and/or a 3'-cap structure, to prevent degradation by exonucleases.

In some embodiments, the VCP inhibitor is a nucleic acid that is at least 90%, at least 91%, at least 92%, at least 93%, at least 94%, at least 95%, at least 96%, at least 97%, at least 98%, or at least 99% identical to the nucleic acids set forth as SEQ ID Nos 1-2.

```
siVCP#1: SEQ ID No: 1: GGAGGTAGATATTGGAATT siVCP#2: SEQ ID No: 2: GGCCAAAGCCATTGCTAAT
```

In some embodiments, the small inhibitory nucleic acid molecules comprise double-stranded nucleic acids containing blunt ends, or overhanging nucleotides. Other nucleotides present may comprise, for example, nucleotides that result in mismatches, bulges, loops, or wobble base pairs. The small inhibitory nucleic acid molecules may be formulated for administration, for example, by encapsulation in liposomes, or by incorporation into other vehicles, such as biodegradable polymers, hydrogels, or cyclodextrins.

Oncolytic Virus

The oncolytic virus (Alphavirus spp. (such as M1 virus and Getah virus), Adenovirus spp., vaccinia virus, measles virus, vesicular stomatitis virus and herpes simplex virus) described herein can include these oncolytic viruses as well as modified forms of these oncolytic viruses, such as forms of these viruses that have undergone natural variation, or mutation (natural or forced or selective), or genetic modification (such as by addition, deletion or substitution of portion(s) of the sequence) that do not affect the oncolytic activity of the viruses. M1 virus belongs to Getah-like virus and its homology with Getah virus is reported to be up to 97.8% in the relevant discovered viruses (Wen et al. Virus Genes. 2007; 35(3):597-603).

For example, information about M1 virus and Getah virus can also refer to Chinese Patent 104814984A.

For example, the oncolytic virus may be the M1 virus as described in Genbank Accession No. EF011023, or may be a virus having a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide sequence set forth in Genbank Accession No. EF011023.

In some embodiment, the oncolytic virus is M1 virus deposited with the China Center for Type Culture Collection on 17 Jul. 2014, and having a deposit number of CCTCC V201423. The oncolytic virus can also have a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide of said M1 with a deposit number of CCTCC V201423.

Further, the oncolytic virus may be a Getah virus as described in Genbank Accession No. EU015062, or may be a virus having a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide sequence set forth in Genbank Accession No. EU015062.

Optionally, a single oncolytic virus strain is used. In other embodiments, multiple strains and/or types of oncolytic virus are used.

Pharmaceutical Composition

The present disclosure also provides a pharmaceutical composition for treating tumors, the composition comprising one or more VCP inhibitors and one or more oncolytic viruses. The present disclosure also provides a pharmaceutical kit for treating tumors, comprising one or more VCP inhibitors and one or more oncolytic virus. The pharmaceutical kit differs from the composition in that in the pharmaceutical kit, the VCP inhibitor is not present in the same dosage form as the oncolytic virus, but is provided in a separate dosage form (such as one pill, or capsule or tablet or ampule comprising the VCP inhibitor(s) and another pill, or capsule or table or ampule comprising the oncolytic virus.) In some embodiments, a dosage form (oncolytic virus, VCP inhibitor or combination oncolytic virus and VCP inhibitor) can also contain one or more adjuvant. Said adjuvant refers to a means that can aid the therapeutic effect of a drug in pharmaceutical composition. A pharmaceutical kit can also contain VCP inhibitor and oncolytic virus that are provided in a separate dosage form. The VCP inhibitor and oncolytic virus in the pharmaceutical kit can be administered simultaneously or in any order, such as where the VCP inhibitor is administered before the oncolytic virus, or the oncolytic virus is administered before the VCP inhibitor, or the VCP inhibitor and the oncolytic virus are administered together. In various embodiments, a patient can refer to a mammal. In some embodiments, the mammal can be a human.

A single VCP inhibitor may be used, or several may be used in combination, concurrently or in series. The VCP inhibitors, and/or the oncolytic virus, may be in the form of compositions comprising one or more inhibitors, and one or more carriers, excipients, diluents, pharmaceutically-acceptable carriers, stabilizers, buffering agents, preservatives, non-ionic detergents, antioxidants, and other additives. The pharmaceutical composition can be administered to a patient by a variety of routes such as orally, transdermally, subcutaneously, intranasally, intravenously, intramuscularly, intrathecally, topically or locally. Typically, the VCP inhibitors will be administered orally, parenterally, intravenously or subcutaneously. The VCP inhibitor may be present in a composition together with the oncolytic virus, or they may be present in separate compositions.

Dosage of VCP Inhibitor and Oncolytic Virus

In various embodiments, the VCP inhibitor (e.g. Eeyarestatin I or NMS-873 or CB-5083) can be present in a range of from 0.01 mg/kg to 200 mg/kg. In some embodiments, a dose of 0.01 to 1 or 1 to 10 or 10 to 100 or 100 to 200 mg/kg can be used. In some preferred embodiments, a dose of Eeyarestatin I, NMS-873 or CB-5083 can be in the range of from 0.1 mg/kg to 200 mg/kg. In some more preferred embodiments, a dose of Eeyarestatin I, NMS-873 or CB-5083 can be in the range of from 1 mg/kg to 200 mg/kg.

In various embodiments, the oncolytic virus can be present in a titer such that MOI (multiplicity of infection) ranges from $10^3$ to $10^9$ (PFU/kg). In some embodiments, a dose providing an MOI of $10^3$ to $10^4$ or $10^4$ to $10^5$ or $10^5$ to $10^6$ or $10^6$ to $10^7$ or $10^7$ to $10^8$ or $10^8$ to $10^9$ PFU/kg can be used. In some preferred embodiments, a dose of oncolytic virus can provide a titer such that MOI ranges from $10^4$ to $10^9$ (PFU/kg). In some other embodiments, a dose of oncolytic virus can provide a titer such that MOI ranges from $10^5$ to $10^9$ (PFU/kg).

In the composition/pharmaceutical kit, the ratio of VCP inhibitor with oncolytic virus may be 0.01~200 mg: $10^3$~$10^9$ PFU (plaque forming units); or preferably 0.1~200 mg: $10^4$~$10^9$ PFU; or more preferably 0.1~100 mg: $10^5$~$10^9$ PFU.

In the composition/pharmaceutical kit, the ratio of Eeyarestatin I or NMS-873 or CB-5083 with oncolytic virus may be 0.01~200 mg: $10^3$~$10^9$ PFU (plaque forming units); or preferably 0.1~200 mg: $10^4$~$10^9$ PFU; or more preferably 0.1~100 mg: $10^5$~$10^9$ PFU. In an embodiment, said oncolytic virus is selected from the group consisting of M1 virus, Getah virus, Adenovirus spp., vaccinia virus, measles virus, vesicular stomatitis virus and herpes simplex virus. Preferably, said oncolytic virus is an M1 virus or a Getah virus.

In various embodiments, the combination of VCP inhibitor and oncolytic virus can be used to treat various types of tumors. Suitable tumors include solid tumors and blood tumors. In some embodiments, said solid tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer. In a preferred embodiment, said tumor is a tumor that is not sensitive to oncolytic virus. In a more preferred embodiment, said tumor is a tumor that is not sensitive to M1 oncolytic virus.

Methods for Treating Tumors

The present disclosure also relates to methods for treating tumors. In some embodiments, one or more VCP inhibitors and one or more oncolytic viruses are administered to a subject having a tumor. The tumor may be a solid tumor or a blood tumor. Preferably, the solid tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer; preferably, the tumor is a tumor that is not sensitive to oncolytic virus; more preferably, the tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer, which is not sensitive to oncolytic virus. The VCP inhibitor may be administered concurrently, before, or subsequent to, administration of an oncolytic virus contemplated herein. Additionally, the VCP inhibitor and/or the oncolytic virus may be administered once a week, or several times (e.g., 2, 3, 4, 5, 6, 7, 8, 9 or 10) a week. The VCP inhibitor and/or the oncolytic virus may be administered for one or several weeks (1, 2, 3, 4, 5, 6, 7, 8, 9, or 10), for a month, or even for several months (2, 3, 4, 5, 6, 7, 8, 9, 10, 11 or 12 or more).

As some embodiments, Eeyarestatin I or NMS-873 or CB-5083 or a combination thereof can be administered by injection or be in the form of a tablet, capsule, patch. In some embodiments, Eeyarestatin I or NMS-873 or CB-5083 or a combination thereof can be part of a kit. In some other embodiments, the combination of VCP inhibitor and oncolytic virus can be administered by injection or preferably by intravenous injection.

In addition, the present disclosure shows that in some embodiments, reduced levels of VCP protein can significantly increase the survival rate of tumor cells treated with oncolytic virus (see Example 4.) The present disclosure also shows that in some embodiments, when the level of VCP (active) is not regulated, the expression of VCP can be positively correlated with the anti-tumor effect of the combination of Eeyarestatin I and oncolytic virus (Example 5), for example, the expression of VCP can affect the anti-tumor effect of the combination of Eeyarestatin I and oncolytic virus. In some embodiments, VCP can be used as a biomarker of the combination of VCP inhibitor and oncolytic virus. The efficacy of anti-tumor effect of the combination of Eeyarestatin I and M1 virus can be closely related to the expression level of VCP in the tumor. VCP can be highly expressed in various tumor cells, and the combination of Eeyarestatin I and oncolytic virus can be used to selectively treat a tumor or individual with high expression level of VCP.

In one embodiment of a method for treating a tumor, the expression of VCP in a tumor of a patient can be firstly determined, then the therapeutic scheme using oncolytic virus can be specifically provided based upon the level of VCP detected. Such an approach can in some embodiments improve the efficacy of the therapeutic scheme and avoid waste of medications and avoid time delay due to ineffective administration of drugs. For example, the expression of VCP in the tumor of a patient can be firstly detected before administration, and in one embodiment where the tumor is of low expression of VCP or is VCP negative, the therapy using oncolytic virus can be directly provided. In another embodiment where the tumor is of normal expression of VCP or high expression of VCP, the VCP inhibitor (for example, VCP expression or function inhibitor, VCP interference fragment, or VCP antibody) can be administered before or at the same time or after the administration of the oncolytic virus, thereby improving sensitivity of the tumor to oncolytic virus and improving efficacy of the therapy. In some embodiments, the expression amount of VCP in the tumor can directly affect the efficacy of the oncolytic therapy. In some embodiments, the lower expression amount of VCP in the tumor can be advantageous for the therapeutic effect of an oncolytic virus. In some embodiments, it can be possible to determine whether a certain individual/tumor is suitable for the therapy using oncolytic virus directly (without the use of a VCP inhibitor) by determining the expression level of VCP in the tumor.

Accordingly, the present disclosure provides an anti-tumor administration system, comprising a VCP detecting reagent or detecting system, and oncolytic virus; said oncolytic viruses can be one or more selected from the group consisting of Alphavirus spp., Adenovirus spp., vaccinia virus, measles virus, vesicular stomatitis virus and herpes simplex virus.

The VCP detecting reagent or detecting system can be any reagent or system that is used for detecting the expression level of VCP. Suitable systems to determine VCP are known and can include, but are not limited to those that operate by determining a genetic or amino acid sequence, and can include those that utilize Western Blot (see Example 4), immunohistochemistry, ELISA, QRT-PCR, etc.

The level of VCP in the tumor can directly affect the efficacy of the combination therapy using VCP inhibitor and oncolytic virus. In some embodiments, a higher level of VCP in the tumor can be more suitable for the following therapeutic scheme: the combination therapy using VCP inhibitor and oncolytic virus. To determine whether a certain individual/tumor is suitable for the combination therapy using VCP inhibitor and oncolytic virus, the expression level of VCP in the tumor can firstly be detected.

In some embodiments, the determination of high, normal, low or negative VCP level can be made by comparing the VCP level of cancerous tissue with the VCP level of related non-cancerous tissue, such as from a non-cancerous portion of the same or a related organ, or from a related type of tissue, such as long muscle for long muscle, bone for bone, etc. In various embodiments, the VCP level can be determined by any method for determining the VCP level of the types of tissue involved. In some embodiments, comparison of the amount of VCP mRNA or VCP protein between two groups of samples or two samples can be performed. If the level of VCP mRNA or VCP protein in one group of tumor samples or one tumor sample is less than or more than that of the other (control) group of samples or the other (control) sample, this group of tumor samples or this tumor sample is called one with low or high expression of VCP, respectively. VCP negative refers to samples with no VCP mRNA or VCP protein in the sample. For testing purposes, a high expression sample would have at least 10%, or at least 20%, or at least 40%, or at least 60%, or at least 80%, or at least 100% more VCP mRNA or VCP protein than the control, a low expression sample would have at least at least 10%, or at least 20%, or at least 30%, or at least 40%, or at least 50%, or at least 60% less VCP mRNA or VCP protein than the control, and a sample with the same expression level (same VCP level) would have a level of VCP mRNA or VCP protein that is between the level of high expression and the level of low expression. A sample VCP negative sample would have a level of VCP mRNA or VCP protein of less than 10%. Samples used for comparison of the amount of VCP mRNA and protein can be: tumor cells vs. normal (control) cells, tumor tissues vs. paracancerous non-neoplastic (control) tissues, or tumors that are effective to the therapy using oncolytic virus vs. tumors that are not effective to the therapy using oncolytic virus (3).

As an optional method, high, low or negative expression of VCP in the tumors means that, the amount of VCP mRNA and/or VCP protein in the tumor tissues is more, less or no expression, compared with that of the corresponding paracancerous non-neoplastic tissues.

If the normalized expression amount of VCP mRNA and protein in the tumor tissues is less than that of the corresponding paracancerous non-neoplastic tissues (in other words, the ratio of the normalized expression amount of VCP in the tumor tissues to that of the paracancerous non-neoplastic tissues is <1), the tumor tissues belongs to those with low expression of VCP. In such situation a combination use of oncolytic virus with VCP inhibitors may not be suitable for treatment.

If the normalized expression amount of VCP mRNA and protein in the tumor tissues is more than that of the corresponding paracancerous non-neoplastic tissues (in other words, the ratio of the normalized expression amount of VCP in the tumor tissues to that of the paracancerous non-neoplastic tissues is >1), the tumor tissues belongs to those with high expression of VCP, and is suitable to be treated by the combination of VCP inhibitor and oncolytic virus (combination therapy). In some embodiments, a combination therapy can be useful and in some embodiments more efficacious than oncolytic virus treatment without the administration of VCP inhibitor. In some other embodiments, a combination therapy (i.e. oncolytic virus and administered VCP inhibitor) can be used for subjects where the ratio of tumor VCP level to paracancerous tissue VCP level is greater than 1.5, or greater than 2, or greater than 2.5, or greater than 3, or greater than 3.5, or greater than 4. In some embodiments, these tumor tissues and these paracancerous non-neoplastic tissues can be tissue samples obtained from pathological puncture or surgical resection or by other suitable means.

In various embodiments, the detection method for VCP mRNA or protein can be any suitable method which is able to quantify or compare VCP levels in tissue, and such methods include but are not limited to those utilizing QRT-PCR, Northern Blot, Western Blot, immunohistochemistry, or ELISA. To accurately determine the difference in the amount of VCP mRNA or protein between different samples, the normalized expression amount of VCP mRNA or protein in each sample are firstly calculated. The normalized expression amount refers to one that is obtained by dividing the value of VCP mRNA or protein in each sample by the value of VCP mRNA or protein in an internal reference of the sample, and conducting a normalized analysis. In different detection methods, the internal reference can be different, and their common characteristics is that the expression amount of internal reference in different cells or tissue samples are identical, so that the expression amount of VCP in different samples through normalized analysis are comparable, for determining difference in the amount of VCP mRNA or protein between the samples.

Preferably, the Alphavirus spp. comprises or consists of at least one selected from M1 virus and Getah virus.

Preferably, the tumor is a solid tumor or a blood tumor.

More preferably, said solid tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer.

In addition, the present disclosure also provides an anti-tumor drug comprising oncolytic virus where the oncolytic virus can be one or more selected from the group consisting of Alphavirus spp., Adenovirus spp., vaccinia virus, measles virus, vesicular stomatitis virus and herpes simplex virus. In some embodiments, this anti-tumor drug can be used for treating a VCP negative tumor or a tumor with low expression of VCP, and in some preferred embodiments, the VCP negative tumor or the tumor with low expression of VCP can be liver cancer, colorectal cancer, bladder cancer, breast cancer, cervical cancer, prostate cancer, glioma, melanoma, pancreatic cancer, nasopharyngeal carcinoma, lung cancer, or gastric cancer.

Preferably, said Alphavirus spp. is at least one selected from M1 virus and Getah virus.

In some embodiments, a tumor to be treated can be a tumor with high expression of VCP, and a combination therapy (such as administration of an oncolytic virus and administration of a VCP inhibitor) can be used. In some preferred embodiments, the tumor can be a VCP negative tumor or a tumor with low expression of VCP, and a therapy using M1 virus alone (without an administered VCP inhibitor) can be used.

In some other embodiments, said tumor can be liver cancer, colorectal cancer, bladder cancer, breast cancer, cervical cancer, prostate cancer, glioma, melanoma, pancreatic cancer, nasopharyngeal carcinoma, lung cancer, or gastric cancer.

In some embodiments, the administration system disclosed herein can improve the administration efficacy of oncolytic virus individually.

An administration system herein refer to, for example, a kit that includes a VCP detecting agent for determining the expression level of VCP in the tumor tissue of an individual, and an anti-tumor drug comprising an oncolytic virus, preferably comprising at least one oncolytic virus and at least one VCP inhibitor. The administration system provided herein allows for a precise treating solution for an individual with a tumor, by firstly determining the VCP expression level of the tumor, before the adoption of a treating solution with an oncolytic virus or a combination use of an oncolytic virus and a VCP inhibitor.

If the tumor cell/tumor tissue of an individual is of VCP high expression, then a treating solution of a combination of oncolytic virus and a VCP inhibitor will be adopted, as according to the present disclosure, such a combination use will result in a better administration efficacy, compared with those of VCP relative low expression. For example, it will result in a much higher rate of tumor cell apoptosis, and/or a much higher tumor-tissue inhibiting rate.

As a further preferred embodiment of the present invention:

As disclosed herein, a VCP inhibitor, preferrably Eeyarestatin I and/or CB-5083, can enhance the anti-tumor effect of oncolytic virus, so as to improve the therapeutic efficacy of oncolytic virus as an anti-tumor drug. As discussed below, cytological experiments demonstrate that M1 virus in combination with Eeyarestatin I and/or CB-5083 could cause a pathological change of tumor cells in terms of morphology, which significantly inhibit tumor cell growth.

When Eeyarestatin I or CB-5083 was administered in combination with M1 virus to human liver cancer Hep3B cell strain, the pathological change of tumor cells in terms of morphology was significantly increased, and the survival rate of tumor cells was significantly reduced. In some cases, the morphological change in tumor cells included cell swelling, nuclear condensation and fragmentation with cells then undergoing apoptosis. For example, in an example of the present invention, when M1 virus (MOI=0.001) was used alone for treating liver cancer cells, the tumor cells had a survival rate of 83.0%. When 5 μM Eeyarestatin I was used alone, the tumor cells had a survival rate of up to 78.2%. However, when 5 μm of Eeyarestatin I or CB-5083 was used in combination with M1 virus having the same MOI, the survival rate of the tumor cells was sharply reduced to 21.6%. In comparison, 5 μM Eeyarestatin I alone resulted in a 12.8% reduction in cell number. Thus, compared with the anti-tumor effect of M1 virus alone, the combination of Eeyarestatin I and M1 produced significantly improved oncolytic effect.

It was disclosed in the Chinese patent CN 201510990705.7 that, when chrysophanol (non-VCP inhibitor anti-tumor synergists for Oncolytic virus) were tested with Oncolytic virus, less efficacy in reducing the survival rate of tumor cells was shown as compared to the combination of VCP inhibitor and Oncolytic virus. For example, when 50 μM chrysophanol was used in combination with M1 virus (MOI=0.001), the survival rate of the tumor cells was 39.6%. When 5 μM Eeyarestatin I or CB-5083 was used in combination with M1 virus (MOI=0.001), the survival rate of the tumor cells was 21.6%. As compared with chrysophanol and the derivative thereof, the Eeyarestatin I or CB-5083 anti-tumor synergist for M1 significantly reduced the survival rate of the tumor cells. In addition, Eeyarestatin I and CB-5083 were used at pharmaceutically effective dose that was merely a tenth of chrysophanol, and acted quickly with a onset time of two thirds of chrysophanol (72 hours for treatment with chrysophanol and 48 hours for treatment with Eeyarestatin I), which resulted in significant advantages.

As presented herein, when Eeyarestatin I or CB-5083 is used in combination with an oncolytic virus to treat tumor cells, the killing effect on tumor cells is significantly higher than that obtained from Eeyarestatin I or CB-5083 alone when used at the same concentration. For example, when tumor cells were treated with 5 μM Eeyarestatin I, the tumor cells had a survival rate of 87.2%. When M1 virus (MOI=0.001) was used alone for treating liver cancer cells, the tumor cells had a survival rate of 83.0%. However, and when 5 μM Eeyarestatin I was used in combination with M1 virus (MOI=0.001), the survival rate of the tumor cells was sharply reduced to 21.6%. Accordingly, greatly increased oncolytic effect was produced by the combination of Eeyarestatin I and M1 by the synergistic action mechanism between Eeyarestatin I and M1, rather than the function produced by the anti-tumor mechanism of Eeyarestatin I.

Discussion of Figures

FIG. 1 shows photographs of microscopic views of sections of liver cells subject to different treatments. Here Eeyarestatin I and M1 virus significantly increase the pathological change of human liver cancer cell strain in terms of morphology.

Figure 2A:
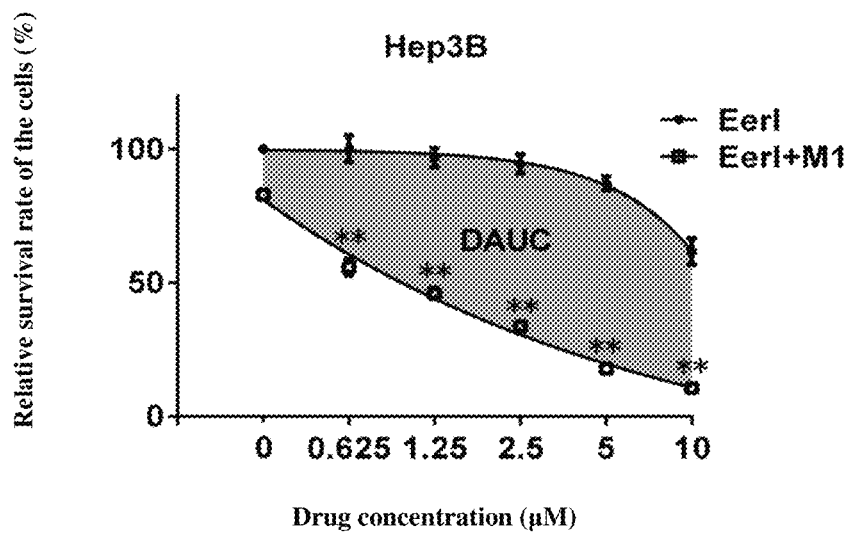
FIGS. 2(A) to 2(B) show graphs of liver tumor cell survival vs. concentration of Eeyarestatin I or CB-5083 with M1.
Figure 2B:
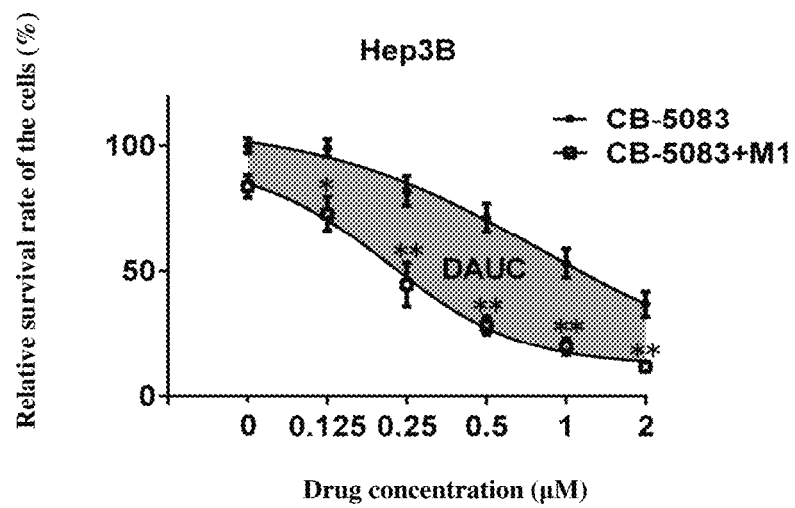

FIGS. 2(A) and 2(B) show graphs of liver tumor cell survival vs. concentration of Eeyarestatin I or CB-5083 with M1 at MOI=0.001. Here, combined treatment of Eeyarestatin I/CB-5083 and M1 virus significantly reduces the survival rate (measured by MTT assay) of human liver cancer cell strain Hep3B. FIG. 2(A) shows that combined treatment of Eeyarestatin I and M1 virus significantly reduces the survival rate of human liver cancer cell strain Hep3B, and FIG. 2(B) shows that combined treatment of CB-5083 and M1 virus can significantly reduce the survival rate of human liver cancer cell strain Hep3B.

Figure 3A:
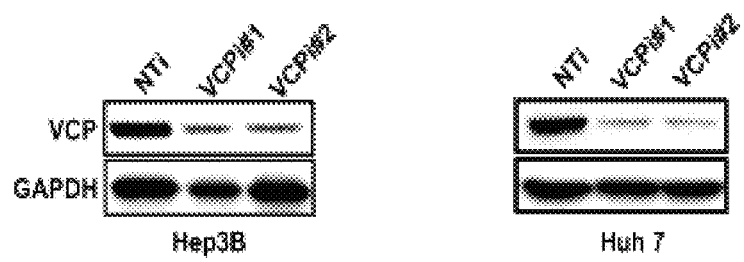
FIGS. 3(A) to 3(C) show various effects of treatment of liver cancer cells with Western Blot.
Figure 3B:
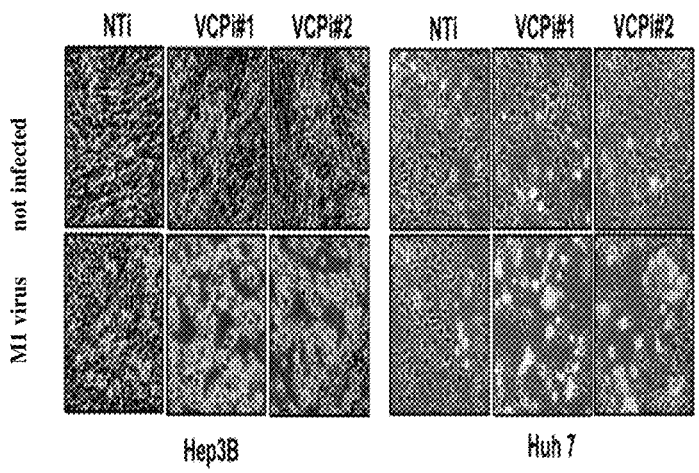
Figure 3C:
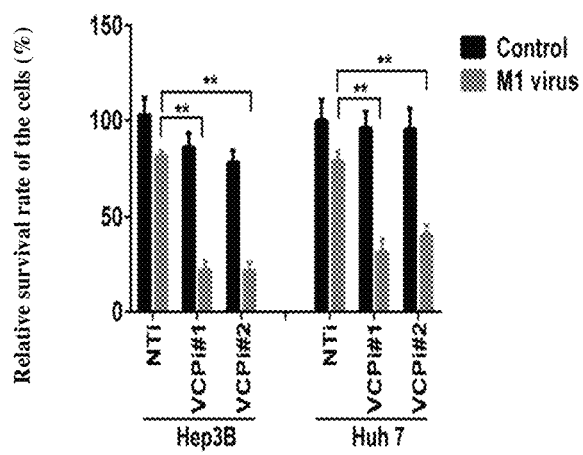

FIG. 3(A) shows a Western blot results of treatment of liver cancer cells with 12.5 μM siRNA targeting VCP. FIG. 3(B) shows pictures of microscopic slides for treatment of liver cancer cells with 12.5 μM siRNA targeting VCP and 0.001 MOI M1 virus. FIG. 3(C) shows graphs of relative survival rate of liver cancer cells treated with 12.5 μM siRNA targeting VCP and 0.001 moi M1 virus. FIGS. 3(A) to 3(C) show that the knockdown of VCP can enhance the oncolytic effect of M1 on liver cancer cells. FIG. 3(A) shows the knockdown of VCP protein from the treatment; FIG. 3(B) shows that the knockdown of VCP can significantly increase the pathological change of human liver cancer cell strain in terms of morphology; and FIG. 3(C) shows that the knockdown of VCP can enhance the oncolytic effect of oncolytic virus M1 on two strains of liver cancer cell.

Figure 4A:
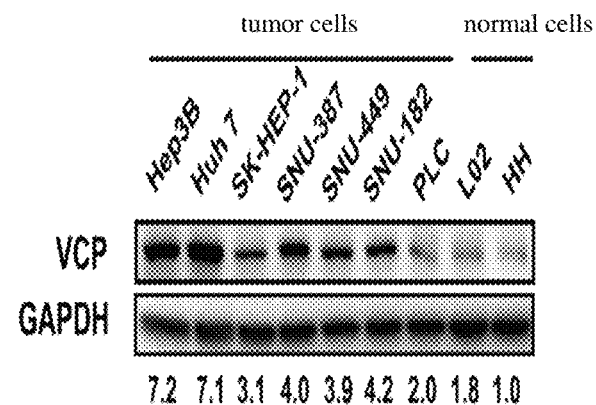
FIGS. 4(A) to 4(D) show various effects of treatment of liver cancer cells with Western Blot.
Figure 4B:
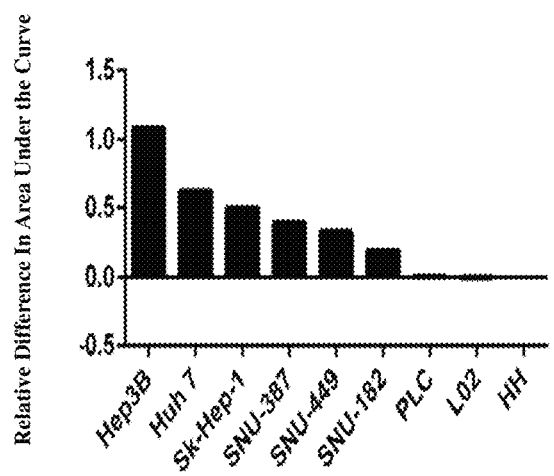
Figure 4C:
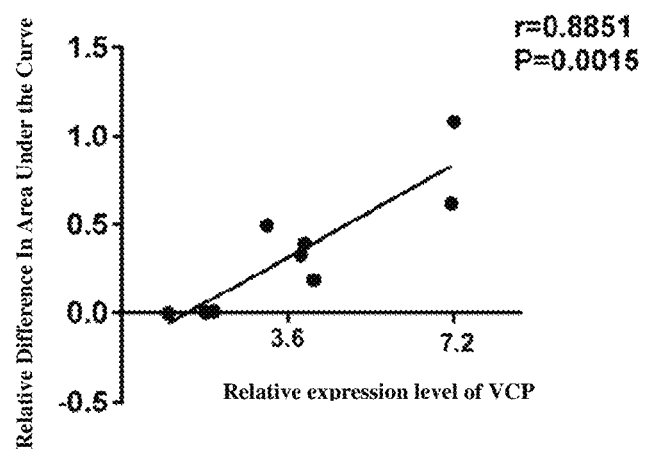

FIG. 4(A) shows a Western blot results of liver cancer cells (background expression). FIG. 4(B) shows a graph of relative differences in area under the curve of VCP concentration vs. time for treatment of different tumor cells. FIG. 4(C) shows a graph of relative difference in area under the curve of VCP concentration over time vs. the relative expression level of VCP. FIGS. 4(A) to 4(C) show the positive correlation between the protein expression of VCP and the anti-cancer effect of the combination therapy using VCP inhibitor and M1 virus. FIG. 4(A) shows the protein expression amount of VCP in a plurality of liver cancer cells and normal cells; FIG. 4(B) shows the effect of the combination of Eeyarestatin I and M1 virus on the survival rate of a plurality of liver cancer cells and normal cells; and FIG. 4(C) shows the correlation analysis of the protein expression of VCP and the combined use of Eeyarestatin I and M1 virus.

Figure 5A:
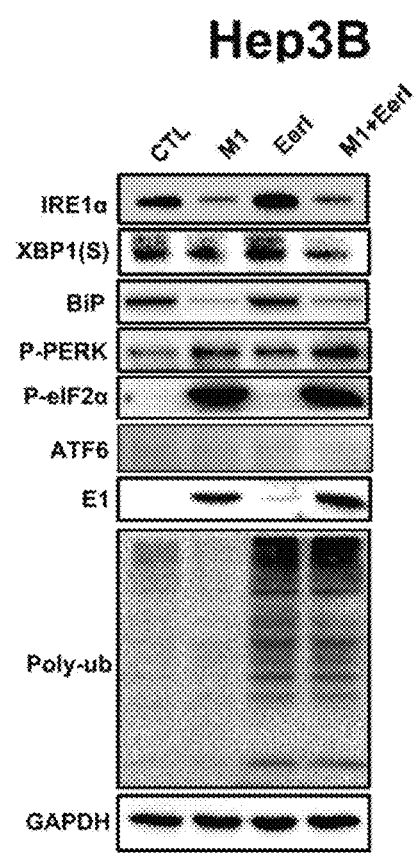
FIGS. 5(A) to 5(B) show with Western Blot results for various treatments of Hep3B cells.
Figure 5B:
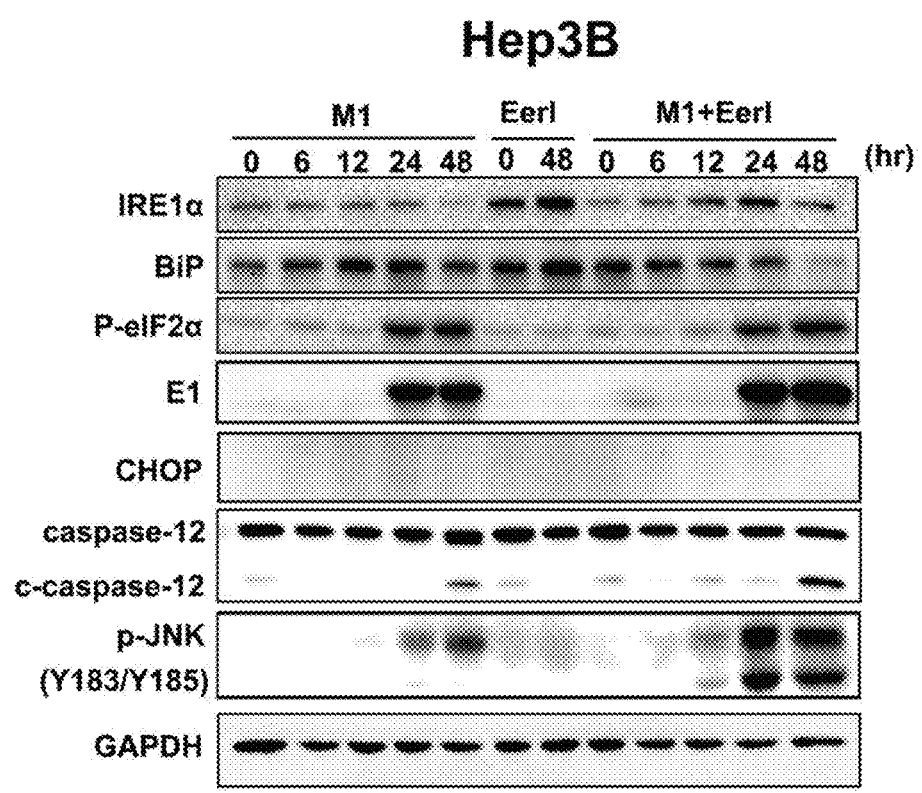

FIGS. 5(A) to 5(B) show that the combination of VCP inhibitor and M1 virus causes tumor cell apoptosis by inducing irreversible endoplasmic reticulum stress. FIG. 5(A) shows that the combination of VCP inhibitor and M1 virus can inhibit the pathway of IRE1-XBP1. FIG. 5(B) shows that the combination of VCP inhibitor and M1 virus can promote endoplasmic reticulum stress-mediated cell apoptosis.

Figure 6A:
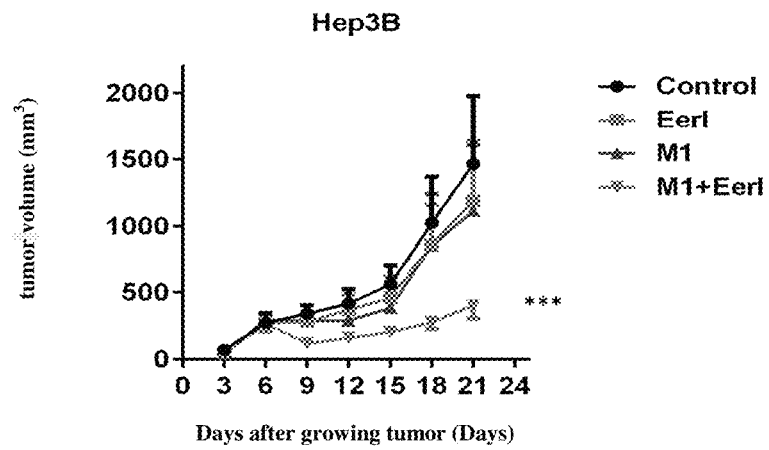
FIGS. 6(A) to 6(D) show graphical and photographic results of treatment of Hep3B and Huh 7 tumors over time.
Figure 6B:
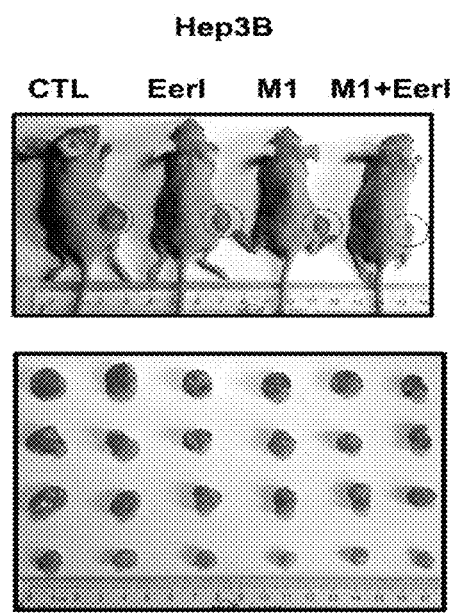
Figure 6C:
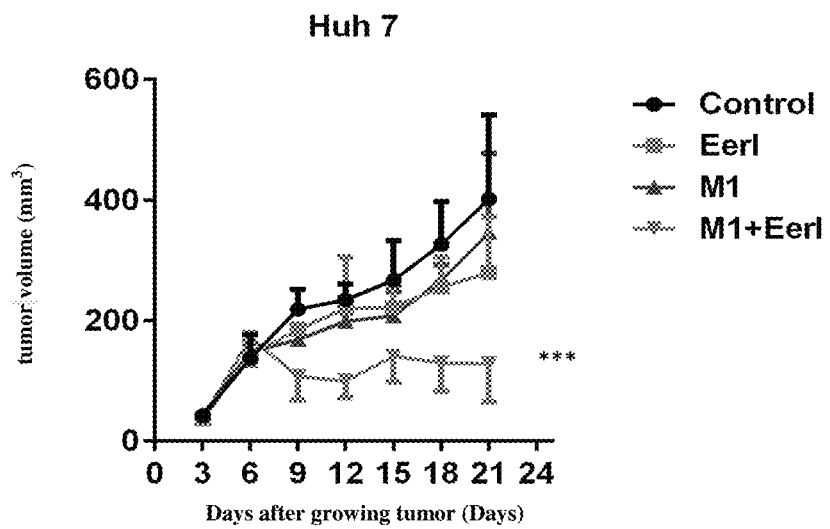
Figure 6D:
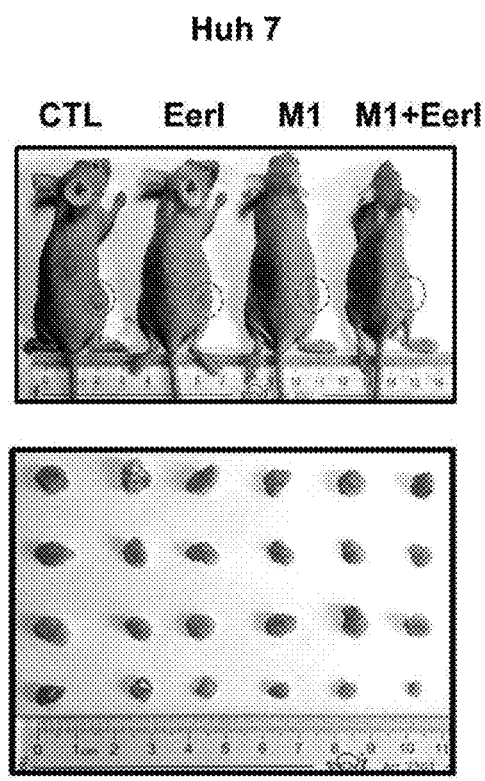

FIGS. 6(A) to 6(D) show that the combined treatment of Eeyarestatin I and M1 virus significantly inhibits the growth of transplantable tumors of human liver cancer cell strain. FIGS. 6(A) and 6(B) show that the combined treatment of Eeyarestatin I and M1 virus significantly inhibits the growth of transplantable tumors of human liver cancer cell strain Hep3B. FIGS. 6(C) and 6(D) show that the combined treatment of Eeyarestatin I and M1 virus significantly inhibits the growth of transplantable tumors of human liver cancer cell strain Huh7.

DESCRIPTION OF SYMBOLS IN THE FIGURES

EerI: a group treated with Eeyarestatin I; CB-5083: a group treated with CB-5083; M1+EerI: a combined treatment group with M1 virus/Eeyarestatin I; M1+CB-5083: a combined treatment group with M1 virus/CB-5083.

EXAMPLES

The present invention is further illustrated by the following Examples. Nevertheless, the embodiments of the present invention are not limited to the following description of the examples. Any equivalent changes or modifications made according to the principle or spirit of the present invention should be deemed as fall within the protection scope of the present invention.

Unless otherwise specified, the materials and experimental methods used in the present invention are conventional materials and methods.

Example 1. Eeyarestatin I and M1 Virus Significantly Increase the Pathological Change of Human Liver Cancer Cell Strain in Terms of Morphology Materials:
Human liver cancer cell Hep3B (purchased from ATCC), M1 virus (obtained with CCTCC V201423), a high glucose-containing DMEM culture medium (4.5 g/l glucose) (purchased from Corning), and an inverted phase contrast microscope.

Methods:

a) Cell cultivation: human liver cancer cell Hep3B was grown in a DMEM (Dulbecco's Modified Eagle's medium) complete culture medium containing 10% FBS (fetal bovine serum), 100 U/ml penicillin and 0.1 mg/ml streptomycin; all the cell strains were placed in a closed incubator with 5% $CO_2$ at 37° C. constant temperature (relative humidity 95%) for subculture. Growth of the cell strains was observed by the inverted microscope. Cells were passaged about every 2-3 days, and the cells in exponential growth phase were taken for a formal experiment.

b) Cell treatment and morphological observation: The cells in exponential growth phase were selected and added into a DMEM complete culture medium (containing 10% fetal bovine serum, 1% penicillin/streptomycin (Life Technologies)) to prepare a cell suspension. The cells were inoculated into a 24-well culture plate at a density of $2.5 \times 10^4$/well. Each well was then treated by addition of Eeyarestatin I (5 µM), M1 virus (MOI=0.001) or Eeyarestatin I (5 µM) plus M1 virus (MOI=0.001) or left untreated as a control. After 48 hours from treatment, the cells were observed by inverted phase contrast microscope for morphological changes.

Results:

As shown in FIG. 1, the morphology of the cells was observed by the phase-contrast microscope. Hep3B cells in the control group were grown in adherent monoculture, and the cells were closely arranged with the uniform phenotype. 48 hours after the treatment with Eeyarestatin I (5 µM) or M1 virus (MOI=0.001) alone, the morphology of the cells was not changed significantly. Nevertheless, 48 hours after the combined treatment with Eeyarestatin I (5 µM) and M1 virus (MOI=0.001), as compared with the cells in the control group and each single treatment group, the number of the viable cells in the combined treatment group was significantly reduced, and the morphology of the viable cells was significantly changed with their cell bodies contracted to a spherical shape, their refractive index significantly increased, and the cells, both viable and dead, showed a morphological sign of death.

Example 2. Combined Treatment of Eeyarestatin I or CB-5083 and M1 Virus Significantly Decreases the Survival Rate of Human Liver Cancer Cell Strain Materials:

human liver cancer cell Hep3B, M1 virus, a high glucose-containing DMEM culture medium, and an automatic microplate reader for enzyme-linked immunosorbent assay. Cells, virus, medium and reagents are from the same sources as Example 1.

Methods:

a) Cell inoculation and administration treatment: The cells in the exponential growth phase from Example 1 were selected and added into a DMEM complete culture medium (containing 10% fetal bovine serum and 1% penicillin/streptomycin (Life Technologies)) to prepare a cell suspension. The cells were inoculated into a 96-well culture plate at a density of $4 \times 10^3$/well. After 12 hours the cells were completely adherent to the wall. The wells were divided into a control group treated without drug and virus, a group treated with Eeyarestatin I or CB-5083 alone, a group infected with M1 alone, and a group treated with the combination Eeyarestatin I and M1 or treated with the combination of CB-5083 and M1. The dose was used as follows: M1 virus (MOI=0.001) that infected the cells; increasing doses of EerI (0, 0.625, 1.25, 2.5, 5, 10 µM) or CB-5083 (0, 0.125, 0.25, 0.5, 1, 2 µM).

b) Reaction of MTT (3-(4,5-dimethylthiazol-2-yl)-2,5-diphenyltetrazolium bromide) with succinate dehydrogenase in the cells as follows: 48 hours after culture, 20 µl MTT (5 mg/ml) was added into each well, and was incubated for further 4 hours. After incubation, granular blue and purple formazan crystals formed in the living cells were observed by microscopic examination.

c) Dissolution of formazan particles formed in the cells was accomplished as follows: the supernatant was carefully sucked off, 100 µl/well DMSO was added to dissolve the formed crystals, and was shaken in a microoscillator for 5 minutes. Then, the optical density (OD value) of each well was detected in an enzyme linked detector at a wavelength of 570 nm. The experiments were repeated for 3 times for each group. The survival rate of the cells=OD value of the drug treatment group/OD value of the control group×100%.

d) Non-linear curve fitting was carried out by using Origin® 8 graphing and analysis software (OriginLab®, Corp., Northampton, Mass., USA), and two dose-response curves (in which one is a dose-response curve of the group treated with Eeyarestatin I or CB-5083 alone and the other is a dose-response curve of the group treated with Eeyarestatin I or CB-5083 and M1 virus) were drawn as FIGS. 2(A) and 2(B), respectively, by taking VCP inhibitor dosage as the x-axis and taking relative survival rate of the cells as the y-axis. The difference in AUC (DAUC) of the two curves was calculated and is shown as shaded in FIGS. 2(A) and 2(B). A greater difference in area under the curve indicates a more significant synergistic effect of the drugs. The relative survival rate of the cells is calculated as in Example 1. Single and double asterisks in FIGS. 2(A) and 2(B) indicate results with one way ANOVA analysis showing a statistical difference with a single asterisk (*) indicating $P<0.05$ and a double asterisk (**) indicating $P<0.01$.

Results:

As shown in FIG. 2(A), treatment with M1 virus (MOI=0.001) alone resulted in a relatively high relative survival rate for Hep3B cells (83.0%), and the tumor cells treated with 5 µM Eeyarestatin I alone had a relative survival rate of 87.2%. However, the Hep3B cells treated with the combination of M1 (MOI=0.001) and 5 µM Eeyarestatin I (Eeyarestatin I+M1) had sharply reduced relative survival rate of 21.6%. Treatment with a higher dose of Eeyarestatin I (10 µM) and M1 virus (MOI=0.001) achieved a further decrease in the relative survival rate of tumor cells Hep3B.

As shown in FIG. 2(B), the treatment with CB-5083 alone also showed significantly higher relative survival rates as compared to the combination of CB-5083 plus oncolytic virus M1 (MOI=0.001) for corresponding CB=5083 concentrations of 0.124 to 2 µM. Accordingly, the presence of VCP inhibitor enhances the oncolytic effect of M1 virus.

Example 3. Knockdown of the Expression Level of VCP could Enhance the Oncolytic Effect of Oncolytic Virus M1 on Liver Cancer Cell Materials:

M1 virus, human liver cancer cell Hep3B, human liver cancer cell Huh7 (purchased from ATCC), RNA interference fragment of VCP (Si RNA) (purchased from Ribobio, referring to SEQ ID Nos 1-2), MTT (purchased from MPbio), Lipofectamine® RNAiMAX (Life Technologies Corp., Carlsbad, Calif., USA) Western blot: total protein extracts of the cells (M-PER™ Mammalian Protein Extraction Reagent, ThermoFisher Scientific, Waltham, Mass., USA), VCP antibody (Cell Signaling Technology, Danvers, Mass., USA) and GAPDH antibody (Cell Signaling Technology, Danvers, Mass., USA). M1 virus, Hep3B and medium are from the same sources as Example 1.

Methods:

The cells were grown as discussed in Example 1 for Hep3B. The cells in the exponential growth phase were selected, and added into a DMEM complete culture medium (containing 10% Fetal bovine serum (GIBICO), 1% penicillin/streptomycin (Life Technologies)) to prepare a cell suspension. The cells were inoculated into a 6-well plate at a density of $1\times10^5$/well. After 24 hours, Si RNA fragment wrapped with RNAiMAX was added. After 48 hours, cells were infected with M1 virus. 48 hours after infection, the samples were treated. Controls were left untreated with Si RNA or RNAiMAX, resulting in an M1 virus treated control and an M1 virus untreated control.

a) 20 μl (5 mg/ml) of MTT was added into each well. After 4 hours, the optical absorbance was determined, and the survival rate of the cells was calculated. The siVCP experimental group was treated with 12.5 μM RNA interference fragment of VCP and the siNC control group was treated with non-targeting siRNAs of VCP (purchased from Ribobio).

b) The protein sample was extracted, and the protein expression of VCP was detected by Western blot, using GAPDH as an internal reference.

c) The experiment was repeated three times, and the data was represented with mean±standard deviation in FIG. 3(C); and statistics of student t test was performed by comparing with the respective control group, wherein  indicates P<0.01 in FIG. 3**(C).

Results:

As shown in FIG. 3(A), after treating human liver cancer cell Hep3B and Huh7 with RNA interference fragment of VCP, the MTT results show the protein expression amount of VCP was significantly reduced.

As shown in FIG. 3(B), the morphology of the cells was observed under the phase-contrast microscope. Hep3B and Huh7 in the control group (labeled "NTi" in FIG. 3(B)) and each group treated with interference VCP (VCPi #1 group and VCPi #2 group) were grown in adherent monoculture, in which the cells were closely arranged with the uniform phenotype, and the morphology of the cells was not changed significantly. Nevertheless, in each combined treatment group, namely treated with interference VCP (VCPi #1 or VCPi #2) and infected by M1 virus (MOI=0.001), the cell number of Hep3B and Huh7 was significantly deceased, and the morphology of the cells was changed significantly, in which their cell body was contracted to a spherical shape, their refractive index was significantly increased, and they showed a pathological sign of death.

As shown in FIG. 3(C), the relative survival rate of the cells subject to combined treatment (interference VCP (VCPi #1 or VCPi #2) plus M1 virus at MOI=0.001), was significantly reduced as compared with the group treated with interference VCP alone (VCPi #1 group and VCPi #2 group). This result was seen for both cells Hep3B and cells Huh7. This difference in relative survival rate was significantly significant with P<0.01 for results marked with double asterisk (**.) After being infected with M1 virus (MOI=0.001), the survival rate of the liver cancer Hep3B cells (VCPi #1 group and VCPi #2 group) after knowdown of the VCP level was significantly decreased to 22.5% and 22.1%, and the survival rate of the liver cancer Huh7 cells (VCPi #1 group and VCPi #2 group) was significantly decreased to 31.8% and 40.8%. The above results showed that knockdown of VCP could enhance the oncolytic effect of oncolytic virus M1 on liver cancer cell.

Example 4. Positive Correlation Between the Protein Expression of VCP and the Anti-Cancer Effect of the Combination Therapy Using VCP Inhibitor and M1 Virus Materials:

M1, human liver cancer cell Hep3B, human liver cancer cell Huh7, human liver cancer cell Sk-Hep-1 (purchased from ATCC), human liver cancer cell SNU-387 (purchased from ATCC), human liver cancer cell SNU-449 (purchased from ATCC), human liver cancer cell SNU-182 (purchased from ATCC), human liver cancer cell PLC (purchased from ATCC), human normal hepatocyte L02 (purchased from ATCC), human primary isolated hepatocyte (HH) (purchased from ScienCell Research Laboratories), Western blot: total protein extracts of the cells (M-PER™ Mammalian Protein Extraction Reagent, ThermoFisher Scientific, Waltham, Mass., USA), VCP antibody (Cell Signaling Technology, Danvers, Mass., USA) and GAPDH antibody (Cell Signaling Technology, Danvers, Mass., USA). M1 virus, Hep3B and medium are from the same sources as Example 1; Huh7 is from the same source as Example 3.

Methods:

The cells were grown as discussed in Example 1 for Hep3B. The cells in the exponential growth phase were selected, and added into a DMEM complete culture medium (containing 10% fetal bovine serum, 1% penicillin/streptomycin (Life Technologies)) to prepare a cell suspension. The cells were inoculated into a 60 mm cell culture dish at a density of $1\times10^6$/well and were cultured for 24 hours.

1. Detection of the Protein Expression of VCP by Western Blot a) Total protein of the cells was extracted and quantified, and Western Blot experiment was carried out (electrophoresis, transmembrane, sealing, incubation of first and second antibodies, and development).

b) The gray levels of straps of VCP and internal reference GAPDH were scanned and detected by Image Lab™ 2.0 software (Bio-Rad, Hercules, Calif., USA), and the normalized protein expression amount of VCP was calculated according to the following formula: the normalized protein expression amount of VCP=the gray level of strap of VCP/the gray level of strap of internal reference GAPDH.

c) The relative protein expression amount of VCP=the normalized protein expression amount of VCP in different cells/the normalized protein expression amount of VCP in HH cells.

2. A dose-response curve with M1 Virus alone and a dose-response curve with the combination of Eeyarestatin I and M1 virus were drawn using a non-linear curve fitting.

a) Cell Inoculation and administration treatment: the cells in the exponential growth phase were selected and added into a DMEM complete culture medium (containing 10% fetal bovine serum and 1% penicillin/streptomycin (Life Technologies)) to prepare a cell suspension. The cells were inoculated into a 96-well culture plate at a density of $4\times10^3$/well. After 12 hours the cells were completely adherent to the wall. The experiment was divided into a control group, a group treated with Eeyarestatin I alone, a group infected with M1, and a group treated with the combination of Eeyarestatin I and M1. The dose was used as follows: Eeyarestatin I (5 µM); different dose gradient for M1 virus.

b) Reaction of MTT with succinate dehydrogenase in the cells: 72 hours after culture, 20 µl (5 mg/ml) MTT was added into each well, and was incubated for further 4 hours. After incubation, granular blue and purple formazan crystal formed in the living cells were observed by microscopic examination.

c) Dissolution of formazan particles: the supernatant was carefully sucked off, and 100 µl/well DMSO was added to dissolve the formed crystal, and was shaken in a microoscillator for 5 minutes. Then, the optical density (OD value) of each well was detected in an enzyme linked detector at a wavelength of 570 nm. The experiments were repeated for 3 times for each group. The survival rate of the cells=OD value of the group treated with drug/OD value of the control group×100%.

d) Non-linear curve fitting was carried out by using Origin 8, and two dose-response curves were drawn for 1) the treatment with Eeyarestatin I alone; and 2) the treatment with the combination of Eeyarestatin I and M1 virus. The difference in AUC of the two curves was calculated and is expressed as multiple unit (i.e., $(AUC_{treatment\ with\ Eeyarestatin\ I\ alone} - AUC_{treatment\ with\ the\ combination\ of\ Eeyarestatin\ I\ and\ M1\ virus})/AUC_{treatment\ with\ the\ combination\ of\ Eeyarestatin\ I\ and\ M1\ virus}$). The greater difference means the more significant synergistic effect of the drugs.

e) The relative AUC and the relative expression of VCP were calculated by the method of pearson correlation analysis, in which r represents the correlation coefficient, if r is more close to 1, it means the greater positive correlation.

Results:

As shown in FIG. 4(A), the bottom of the picture of Western blot showed the relative protein expression amount of VCP in different cells, indicating that the protein expression level of VCP was different in different cells. The expression amount of VCP in human liver cancer cell Hep3B and Huh7 was more than 7 times that of human primary normal cell HH; the expression amount of VCP in human liver cancer cell Sk-Hep-1, SNU-387, SNU-449, or SNU-182 were more than 3 times that of human primary normal cell HH; and the expression amount of VCP in human liver cancer cell PLC was twice that of human primary normal cell HH.

Figure 4D:
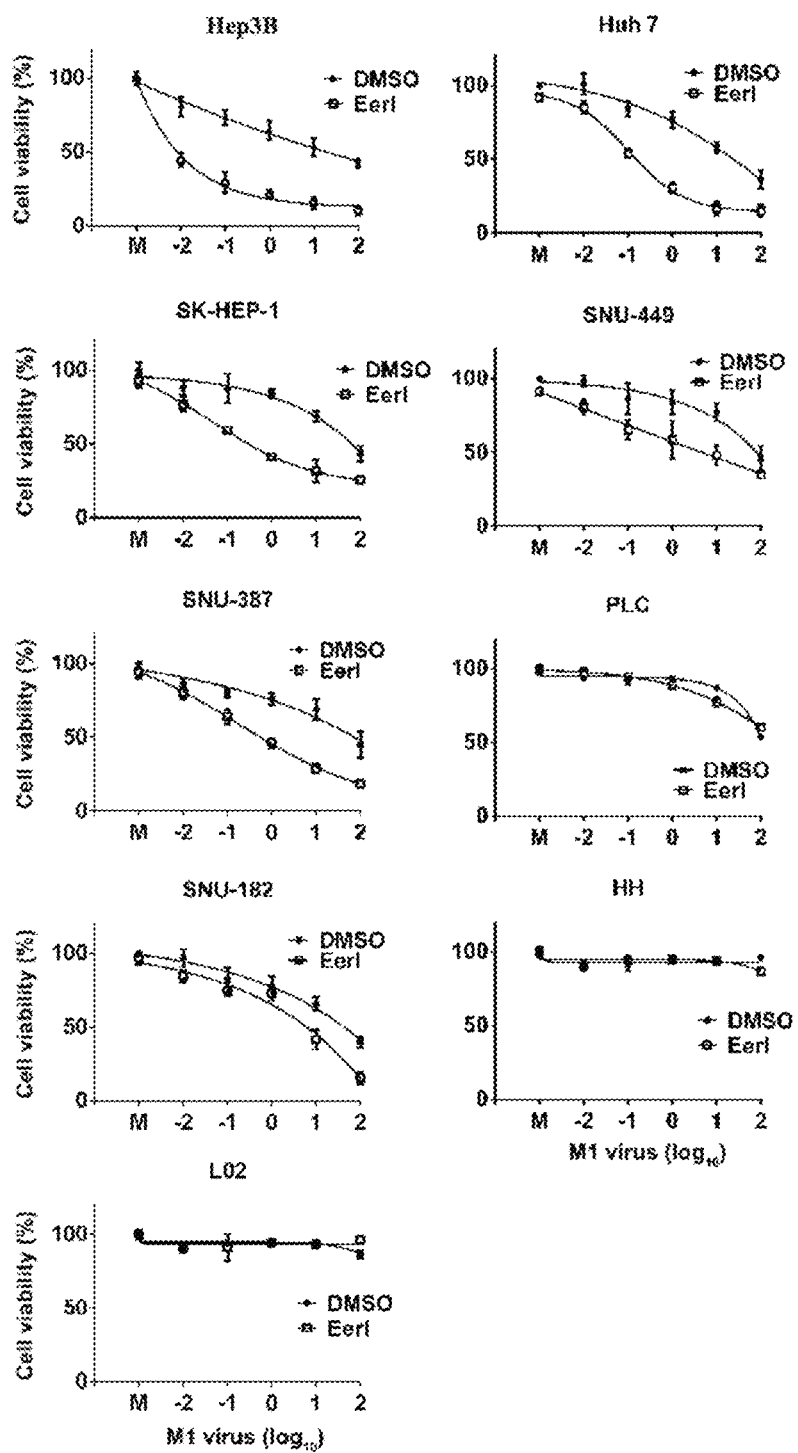

As shown in FIGS. 4(B) and 4(D), in which two dose-response curves were drawn, non-linear curve fitting was carried out by using Origin 8, and the relative DAUC (Difference in area under the curve) values were determined and graphed, in the tumor cells was significantly higher than that of the normal cells, a fact which showed that the combination of Eeyarestatin I and M1 virus achieved increased killing effect in the tumor cells with high expression of VCP, but had no significant effect on the survival rate of the normal cells with low expression of VCP.

As shown in FIG. 4(C), according to the statistics of the method of Pearson correlation analysis, it was found that the expression of VCP is positively correlated with the effect of the combination therapy using Eeyarestatin I and M1 virus. Therefore, the protein expression of VCP is positively correlated with the anti-cancer effect of the combination therapy using VCP inhibitor and M1 virus. This showed that VCP could be used as a biomarker for the suitability of treatment with the combination of VCP inhibitor and M1 virus.

Example 5. The Combination of VCP Inhibitor and M1 Oncolytic Virus Causes Tumor Cell Apoptosis by Inducing Irreversible Endoplasmic Reticulum Stress Materials:

M1 virus, human liver cancer cell Hep3B, monoclonal antibodies (IRE1(3294s, Cell Signaling Technology), XBP1 (S) (12782s, Cell Signaling Technology), BiP (3177s, Cell Signaling Technology), p-PERK (sc-32577, Santa Cruz Biotechnology), p-eIF2a (3398s, Cell Signaling Technology), ATF6 (sc-22799, Santa Cruz Biotechnology), poly-ub (3933s, Cell Signaling Technology), GAPDH (AP0060; Bioworld), caspase-12 (ab62484, Abcam), CHOP (2895s, Cell Signaling Technology), p-JNK (9255s, Cell Signaling Technology)). M1 virus and Hep3B are from the same source as for Example 1.

Method:

The cells were grown as discussed in Example 1 for Hep3B. The cells in the exponential growth phase were selected and added into a DMEM complete culture medium to prepare a cell suspension. The cells were inoculated into a 60 mm culture dish at a density of $1\times10^6$. After 12 hours the cells were completely adherent to the wall. The experiments was divided into a control group, a group treated with Eeyarestatin I alone, a group infected with M1, and a group treated with the combination of Eeyarestatin I and M1. The dose was used as follows: M1 virus (MOI=0.001) that infected cells; Eeyarestatin I (5 µM).

After the time of drug treatment was set up, the protein samples were collected to carry out the Western blot for detecting the marker of endoplasmic reticulum stress (IRE1 XBP1(S), BiP, p-PERK, p-eIF2a, ATF6, poly-ub); and the activation of the pathway of endoplasmic reticulum stress-associated apoptosis (caspase-12, CHOP, p-JNK). The results of the Western blot testing are shown in FIGS. 5(A) and 5(B).

Results:

The use of Eeyarestatin I (5 µM) alone could up-regulate the endoplasmic reticulum stress-associated unfold protein response pathway, as shown in FIG. 5(A), Eeyarestatin I (5 µM) could induce the increase of endoplasmic reticulum stress-associated markers such as IREI, XBPI (S), p-PERK, p-eIF2a. The use of oncolytic virus M1 (MOI=0.001) alone could inhibit IREI, XBPI (S), without affecting other pathways. We observed that when Eeyarestatin I (5 µM) was used in combination with M1 virus, M1 virus could block the up-regulation of IREI and XBPI pathway caused by Eeyarestatin I, thereby promoting the intense endoplasmic reticulum stress, activating caspase-12 and JNK pathway (FIG. 5(B)), and inducing cell apoptosis.

Example 6. The Combination of Eeyarestatin I and M1 Virus Significantly Inhibits the Growth of Transplantable Tumors of Human Liver Cancer Cell Strain Materials:

M1 virus, human liver cancer cell strain Hep3B, human liver cancer cell strain Huh7, 4-week-aged female BALB/c nude mice (Model animal research center of Nanjing University). M1 virus and Hep3B are from the same source as for Example 1; Huh7 is from the same source as in Example 3.

Methods:

A randomized, single-blind study was conducted. For each subject mouse, 5×10⁶ Hep3B or Huh7 cells were subcutaneously injected into dorsa of the 4-week-aged BALB/c nude mice.

When the size of the tumors reached 50 mm³, the mice were divided into groups, including an untreated control group, a group treated with Eeyarestatin I alone (i.p. 2 mg/kg/d), a group infected with M1 alone (tail vein injection with M1 virus of 5×10⁵ PFU/time), and a group treated with the combination of Eeyarestatin I and M1 (Eeyarestatin I and M1 virus were administered in the same way at the same dose as for the Eeyarestatin I alone and the M1 alone), and six injections was performed continuously (Six injections was performed on days 6-8, and days 12-14). The weight, length and width of the tumor were measured every two days, and the volume of the tumor was calculated according to the formula: (length×width²)/2. After measuring the volume of the tumor, One way ANOVA statistics was carried out, wherein *** indicates p<0.001.

Results:

Pathological anatomy was carried out in the animals with transplantable tumors of human liver cancer cell strain Hep3B and human liver cancer cell strain Huh7 to measure the volume of the tumors. The results showed that as compared with the control group, the group treated with Eeyarestatin I alone and the group infected with M1 alone could only cause slight shrinkage of tumor volume, while the group treated with the combination of Eeyarestatin I and M1 could cause significant shrinkage of tumor volume (see FIGS. 6(B) and 6(D)). At the end of the experiment using the model of human liver cancer cell strain Hep3B, the tumor volume in the control group was 1463.6 mm², the tumor volume in the group treated with Eeyarestatin I alone and the group infected with M1 alone was 1189.7 mm² and 1117.5 mm², respectively, and the tumor volume in the group treated with the combination of Eeyarestatin I and M1 combined was 404.3 mm². At the end of the experiment using the model of human liver cancer cell strain Huh 7, the tumor volume in the control group was 401.6 mm², the tumor volume in the group treated with Eeyarestatin I alone and the group infected with M1 alone was 279.5 mm² and 346.2 mm², respectively, and the tumor volume in the group treated with the combination of Eeyarestatin I and M1 was 128.3 mm². One way ANOVA statistics showed that there was a statistical difference (FIGS. 6(A) and 6(C)).

The above-described examples are only illustrative embodiments of the present invention. Nevertheless, the embodiments of the present invention are not limited to the above-described examples. Any other change, modification, replacement, combination, and simplification without departing from the spirit and principle of the present invention are all included in the protection scope of the present invention.

1. S. Yamamoto, Y. Tomita, S. Nakamori, Y. Hoshida, H. Nagano, K. Dono, K. Umeshita, M. Sakon, M. Monden, K. Aozasa, Elevated expression of valosin-containing protein (p97) in hepatocellular carcinoma is correlated with increased incidence of tumor recurrence. *J Clin Oncol* 21, 447-452 (2003).
2. Y. Tsujimoto, Y. Tomita, Y. Hoshida, T. Kono, T. Oka, S. Yamamoto, N. Nonomura, A. Okuyama, K. Aozasa, Elevated expression of valosin-containing protein (p97) is associated with poor prognosis of prostate cancer. *Clin Cancer Res* 10, 3007-3012 (2004).
3. K. Li, H. Zhang, J. Qiu, Y. Lin, J. Liang, X. Xiao, L. Fu, F. Wang, J. Cai, Y. Tan, W. Zhu, W. Yin, B. Lu, F. Xing, L. Tang, M. Yan, J. Mai, Y. Li, W. Chen, P. Qiu, X. Su, G. Gao, P. W. Tai, J. Hu, G. Yan, Activation of Cyclic Adenosine Monophosphate Pathway Increases the Sensitivity of Cancer Cells to the Oncolytic Virus M1. *Mol Ther* 24, 156-165 (2016).

The invention claimed is:

1. A pharmaceutical composition or a kit, comprising: at least one Valosin containing protein (VCP) inhibitor; and at least one oncolytic virus, wherein the oncolytic virus is Alphavirus M1 (M1 virus) and the Valosin containing protein (VCP) inhibitor is selected from the group consisting of Eeyarestatin I, NMS-873, CB-5083, RNA interference fragment of VCP (siRNA) and a combination thereof.

2. The pharmaceutical composition or the kit according to claim 1, wherein said tumor is a solid tumor or a blood tumor.

3. The pharmaceutical composition or the kit according to claim 1, wherein the ratio of Eeyarestatin I, NMS-873, CB-5083 or RNA interference fragment of VCP (siRNA) with said M1 virus is 0.01~200 mg: $10^3$~$10^9$ PFU.

4. The pharmaceutical composition or the kit according to claim 1, wherein said pharmaceutical composition or the kit further comprises a pharmaceutically acceptable carrier.

5. A method for treating a subject with a tumor, comprising: administering to the subject at least one oncolytic virus; and enhancing an anti-tumor effect of said oncolytic virus comprising administering to the subject in need thereof at least one VCP inhibitor, wherein the oncolytic virus is Alphavirus M1 (M1 virus) and the Valosin containing protein (VCP) inhibitor is selected from the group consisting of Eeyarestatin I, NMS-873, CB-5083, RNA interference fragment of VCP (siRNA) and a combination thereof.

6. The method of claim 5, wherein the tumor is a solid tumor or a blood tumor.

7. The pharmaceutical composition or the kit according to claim 1, wherein said solid tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer; or
said tumor is a tumor that is not sensitive to oncolytic virus; or said tumor is a tumor with high expression of VCP.

8. The method of claim 5, wherein said tumor is liver cancer, colorectal cancer, bladder cancer, breast cancer, cervical cancer, prostate cancer, glioma, melanoma, pancreatic cancer, nasopharyngeal carcinoma, lung cancer, or gastric cancer; or
said tumor is a tumor that is not sensitive to oncolytic virus.

9. The pharmaceutical composition or the kit according to claim 1, wherein said M1 virus
has a genome as described in Genbank Accession No. EF011023, or has a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide sequence set forth in Genbank Accession No. EF011023; or
has at least 80%, at least 85%, at least 90%, at least 91%, at least 92%, at least 93%, at least 94%, at least 95%, at least 96%, at least 97%, at least 98%, or at least 99% nucleotide sequence identity to the genome of the M1 virus deposited under Accession No. CCTCC V201423.

10. The pharmaceutical composition or the kit according to claim 1, wherein the VCP inhibitor is Eeyarestatin I.

11. The method of claim 5, wherein the VCP inhibitor is Eeyarestatin I.

12. The method of claim 5, wherein said M1 virus
has a genome as described in Genbank Accession No. EF011023, or has a genome that is at least 80%, at least 85%, at least 90%, at least 91%, at least 92%, at least 93%, at least 94%, at least 95%, at least 96%, at least 97%, at least 98%, or at least 99%, identical to the genomic nucleotide sequence set forth in Genbank Accession No. EF011023; or
has at least 80%, at least 85%, at least 90%, at least 91%, at least 92%, at least 93%, at least 94%, at least 95%, at least 96%, at least 97%, at least 98%, or at least 99% nucleotide sequence identity to the genome of the M1 virus deposited under Accession No. CCTCC V201423.

* * * * *

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Synthetic sequence

<400> SEQUENCE: 1
ggaggtagat attggaatt                                              19

<210> SEQ ID NO 2
<211> LENGTH: 19
<212> TYPE: DNA
<213> ORGANISM: Artificial Sequence
<220> FEATURE:
<223> OTHER INFORMATION: Synthetic sequence

<400> SEQUENCE: 2
ggccaaagcc attgctaat                                              19
```